United States Patent [19]
Glazer et al.

[11] Patent Number: 5,277,869
[45] Date of Patent: Jan. 11, 1994

[54] PROCESS AND SYSTEM FOR BIOLOGICALLY NEUTRALIZING WASTE MATERIAL

[75] Inventors: Sanford A. Glazer, Potomac, Md.; Robert S. Russell, Orlando, Fla.; Bernard Cole, Northbrook, Ill.

[73] Assignee: Medical Waste Tech, Inc., Rockville, Md.

[21] Appl. No.: 8,870

[22] Filed: Jan. 25, 1993

Related U.S. Application Data

[63] Continuation of Ser. No. 772,094, Oct. 3, 1991, abandoned.

[51] Int. Cl.⁵ .......................... A61L 2/06; B02C 23/22
[52] U.S. Cl. ........................................ 422/26; 422/32; 422/33; 422/108; 422/287; 422/309; 588/258; 588/900; 241/17; 241/606; 241/46.17
[58] Field of Search ................. 422/26, 32, 33, 38, 422/108, 184, 286, 287, 309; 241/606, 15, 17, 23, 46.17, 65; 588/258, 900

[56] References Cited

U.S. PATENT DOCUMENTS

| | | | |
|---|---|---|---|
| 3,589,276 | 6/1971 | Swallert | 100/90 |
| 3,762,874 | 10/1973 | Berry | 422/38 X |
| 4,037,795 | 7/1977 | Fyfe | 241/58 |
| 4,623,515 | 11/1986 | Frei et al. | 422/1 |
| 4,905,916 | 3/1990 | Sorwick et al. | 241/23 |
| 4,917,310 | 4/1990 | Carrera | 241/DIG. 38 X |

(List continued on next page.)

FOREIGN PATENT DOCUMENTS

| | | | |
|---|---|---|---|
| 0054823 | 6/1982 | European Pat. Off. | |
| 3705364 | 5/1988 | Fed. Rep. of Germany | 422/184 |
| 9003949 | 4/1990 | PCT Int'l Appl. | |
| 9014890 | 12/1990 | PCT Int'l Appl. | 241/DIG. 38 |

OTHER PUBLICATIONS

The Safe Drinking Water Act, as amended by The Safe Drinking Water Act Amendments of 1986, Pub.; L. No. 99-339 (1986).

"Council Report-Infectious Medical Wastes", Journal of the American Medical Association (JAMA), vol. 262, No. 12, pp. 1669-1671 (Sep. 22/29, 1989).

F. Cross, "Siting a Medical Waste Treatment Facility", Pollution Engineering, Sep. 1990, pp. 68-73.

Brochure, Medical SafeTEC, Inc., Z-5000 Infectious Waste Disposal Specifications and Indiana University Scholl of Medicine Report dated Apr. 3, 1984.

M. French and H. Eitzen, "Report on the Microbiologic Effectiveness of the Medical Safe Tec Waste Management System", Indiana University Dept. of Hospital Infection Control, Apr. 1984.

(List continued on next page.)

Primary Examiner—Robert J. Warden
Assistant Examiner—T. A. Trembley
Attorney, Agent, or Firm—Venable, Baetjer, Howard & Civiletti

[57] ABSTRACT

A process and processing system are disclosed that provide for the processing of many forms of waste, such as medical and food waste, that both reduces the volume of waste solids and neutralizes the biological activity of such waste, thereby facilitating the disposal of potentially unhealthy or hazardous materials. Biological neutralization is accomplished by chopping the waste material and mixing it with a circulating stream of fluid such as water that is superheated to a temperature which effects disinfection or sterilization in accordance with the needs of the user. The superheated fluid is maintained substantially in a liquid form to facilitate intermixing with the waste material and absorption thereby in instances of the processing of fluid-absorbable materials. The processed waste can be filtered to remove solid particles having a size in excess of a predetermined amount, and the filtrate can be passed into municipal sewer systems. The filtered solids can be disposed of in a conventional manner, as by disposal in land fills, burial, or incineration.

42 Claims, 8 Drawing Sheets

U.S. PATENT DOCUMENTS

| | | | |
|---|---|---|---|
| 5,035,367 | 7/1991 | Nojima | 241/37.5 |
| 5,048,766 | 9/1991 | Gaylor et al. | 241/DIG. 38 X |
| 5,087,420 | 2/1992 | Jackson | 422/37 |
| 5,089,228 | 2/1992 | Meijer | 241/DIG. 38 X |
| 5,119,994 | 6/1992 | Placzek | 422/309 X |

OTHER PUBLICATIONS

National Primary Drinking Water Regulations Fact Sheet, United States Environmental Protection Agency (1991).

IARC Monographs of the Evaluation of Carcinogenic Risks to Humans, Jun. 12-19, 1990, World Health Organization Int'l Agency for Research on Cancer (IARC), vol. 52, pp. 32-35, 37-39, 520-521, 1991.

S. Krasner, et al., "The Occurrence of Disinfection By-Products in US Drinking Water", Journal of the American Water Works Association (AWWA), Aug. 1989, pp. 41-45.

W. Rutala, et al., "Management of Infectious Waste by US Hospitals", Journal of the American Medical Association (JAMA), vol. 262, No. 12, pp. 1635-1640 (Sep. 22/29, 1989).

PROCESS AND SYSTEM FOR BIOLOGICALLY NEUTRALIZING WASTE MATERIAL

This application is a continuation of application Ser. No. 772,094, filed Oct. 3, 1991, now abandoned.

BACKGROUND OF THE INVENTION

1. Field of the Invention

The invention relates generally to waste disposal method and apparatus, and more particularly to method and apparatus for effecting disinfection, and optionally sterilization, of waste materials such as medical, food and other types of waste.

2. Description of the Related Art

Waste management has evolved in the latter part of the twentieth century into an industry of considerable importance, as societal and environmental attention has focused on the conventional processes by which waste has to date been handled for disposal. These conventional waste disposal processes include incineration, dumping at sea, and burial in landfills. Each of these processes, however, is encumbered by significant societal and environmental disadvantages. Incineration is objectionable due to its attendant chemical and particulate pollution of the atmosphere and surrounding locales. Further, these pollutants can be transported over great distances by prevailing winds, thereby extending the scope of environmental impact beyond the immediate locale of the incinerator. Waste disposal in the oceans is objectionable due to its adverse environmental impact on sea life and coastal shores. Landfills are objectionable due to their attendant spatial demands, offensive odors, and potential for production of hazardous substances arising from the mixing and interaction of buried materials. Spatial considerations are especially prevalent in urban centers, where population growth has resulted in suburban expansion to locations well outside of the urban center, necessitating in some instances in the relocation of existing landfills and the creation of costly new landfills at locations geographically remote from the centers they serve.

Further waste disposal problems arise in view of the type of waste that is to be disposed. For example, special precautions are required for the disposal of biological and medical waste due to the overwhelming concern for preventing the creation and/or spread of infectious disease. Further concerns arise due to the presence of extremely sharp medical instruments such as needles, knives, and broken glass containers that can cut or lacerate the skin of personnel and animals with which the waste comes in contact, thereby presenting both a risk of physical harm and biological contamination. For these reasons, such waste is typically thermally or chemically treated and buried in dedicated medical waste disposal facilities. The treatment can be of a type that results in disinfection, and optimally sterilization, of the waste so as to render it biologically neutral or inert. As used in the description which follows, the term "disinfection" and its variants pertains to the destruction of pathogenic microorganisms or their toxins or vectors, whereas "sterilization" and its variations pertains to the destruction of all living microorganisms and their spores, thereby rendering the material so processed void of all living matter.

Sterilization can typically be accomplished by any one of a variety of prescribed chemical and noncombustion thermal treatment regimens, as well as incinerarion. Chemical sterilization generally provides for exposure of the waste material to an antiseptic solution such as liquid chlorine for a prescribed time interval; however, the use of chemical sterilizing agents presents disposal problems for the liquid following waste treatment due to the toxicity of chlorine and other antiseptic solutions. A popular alternative to chemical disinfection is autoclaving, which provides for exposure of the waste to heat at upwards of 250° F. (121° C.) at 15 psi for 15–40 minutes. While sterilization can be accomplished in both dry air and steam environments, steam autoclaving is generally preferred due to its greater penetrating capabilities (especially important for sterilizing "soft" waste such as textiles and gauze) and its lethality via the process of denaturation. Longer periods are used to assure steam penetration of heavy, fluid-absorbable loads. Faster processing can be accomplished for some waste materials by increasing temperature and pressure. However, a significant disadvantage of steam autoclaving is its failure to assure complete penetration of the waste and its exposure to the heat contained within the water vapor. Further disadvantages include the tendency for autoclaves (both steam and dry) to stratify and to trap comparatively cool air in pockets, thereby precluding sterilization. In addition, the waste is neither reduced in volume or in mass; instead, mass can increase in some instances (i.e., textiles and gauze) due to the absorption of water vapor, thereby exacerbating the problem of waste disposal referenced above.

In view of the foregoing, there is a pressing societal need to not only reduce the quantity of waste material that is produced, but also to more effectively and efficiently process the waste so that it has a diminished environmental impact. While efforts are being undertaken to reduce waste production, these efforts alone will not eliminate the various problems associated with waste disposal, particularly in the medical and dental industries, where single patient use (i.e., non-reusable) surgical instruments have gained widespread acceptance due to concerns over spread of the family of hepatitis viruses and HIV. Accordingly, the present invention is directed to providing methods and apparatus for disinfecting, and optimally sterilizing, medical and other forms of waste and reducing the volume of waste solids for disposal. These and other objects and advantages of the present invention will become apparent from the following specification when read in conjunction with the accompanying drawings.

SUMMARY OF THE INVENTION

The invention is directed to methods and apparatus for disinfecting, and optimally sterilizing, non-toxic waste and for reducing the volume of waste solids, thereby simplifying procedures for waste disposal and reducing the demand for disposal space in landfills. While the invention is particularly advantageous for use in processing medical waste, its principles are equally applicable for the treatment of other forms of waste, such as food waste produced incident to the operation of restaurants and so-called "fast food" establishments. In this latter regard, waste treatment in accordance with the teachings of the present invention greatly reduces the organic content of the waste solids, thereby resulting in a diminution of rodent and other pest infestation typically associated with food waste disposal as well as the capacity requirements for waste receptacles (i.e., "dumpsters") on-site at the restaurant.

In a preferred aspect of the invention, a closed, pressurized waste processing system is provided that is operable to effect biological neutralization of waste by a process of waste sterilization. As used herein, the term "system" includes both methods and apparatus for effecting the desired form of waste treatment. The system provides for receipt of the waste in a decontamination chamber which is sealable by a removable and pressurizable cover. A reservoir is provided and is operable through appropriate valve apparatus to deliver water or other suitable fluids to the flow of waste material as it is drawn toward a waste processing chopper/pump assembly positioned downstream from the decontamination chamber. Preferably, the fluid is water and is stored within the reservoir at an elevated temperature of on the order of about 170° F. (77° C.) so as to expedite processing. A selectively-actuable gate can be provided in the line between the decontamination chamber and the chopper/pump to inhibit the flow of waste solids to the chopper/pump until it attains its optimal operating speed, at which point the gate can be opened to permit the fluid and solids stored in the chamber to flow to the chopper/pump for processing thereby. Output from the pump is directed to the decontamination chamber and circulates therethrough in a closed, pressurized circuit in a continuous manner, during which time the waste solids are ground by the chopper/pump to successively finer particles and mixed with the circulating fluid from the reservoir. Suitable heating means is associated with the decontamination chamber to effect heating of the fluid and entrained waste solids to the requisite temperature to effect disinfection or sterilization as these materials are circulated by the pump for the desired period of time. Sterilization can be implemented by elevating the temperature of the circulating waste and fluid mixture to a temperature of at least 270° F. (132° C.) and maintaining that temperature for a time interval of at least six minutes. Temperature sensors are preferably provided along the fluid flow path to provide an indication of circulated fluid temperature throughout system operation and to ensure that the requisite processing temperature has been maintained for the required time interval. Once the waste material has been ground by the pump and exposed to the heated water for the prescribed period of time, the water and entrained waste particulates are directed to a receiving tank that is substantially filled with tap water at ambient temperature for cooling to a prescribed minimum temperature so as to permit for disposal of the liquid portion of the mixture into the municipal waste disposal system. Cooling of the processed waste can be expedited by introducing cool water from the receiving tank into the circulating stream of sterilized waste material. Although the waste will no longer be "biologically neutral" following its mixture with the tap water, the waste material will nevertheless be biologically and physically safe for disposal, as it will have a biological activity attributable only to that of the tap water with which it is mixed. The ground waste solids can be filtered from the processed waste and disposed of in a conventional manner, whereas the waste liquids can be passed (following cooling) into the municipal sewer lines.

In a further aspect of the invention, waste processing in the foregoing manner is electronically controlled in accordance with a pre-established system program. However, variables such as pump speed, fluid flow rate and duration of operation can be selected within prescribed ranges in accordance with such factors as the nature and quantity of waste to be treated. Further parameters which affect waste processing include the dimensions of the conduits through which processed material and fluid flow. Preferably, the foregoing variables and parameters are selected to provide for the production of processed waste solids of a size in the range of from about 1/16 in. (1.5 mm) to about ¼ in. (6.5 mm) in their largest dimension. A printout of system operation parameters such as waste temperature throughout the processing procedure can optionally be provided to render a permanent record of system operation. Alternatively, or in conjunction with printer operation, the various above-referenced operation parameters can be stored in electronic memory for subsequent recall and display on a visually perceptible device such as a cathode ray tube (CRT) or similar display of alphanumeric and graphic data. In all instances, however, waste processing proceeds for a period of time which provides for grinding and exposure of the waste to a circulating stream of superheated water for a period of time that meets or exceeds the applicable standards and regulations governing material disinfection and sterilization in accordance with the selected form of waste treatment.

BRIEF DESCRIPTION OF THE DRAWINGS

The various objects and advantages of the subject invention will become more apparent from a reading of the following drawing figures, in which.

FIG. is a side view of a waste processing apparatus in accordance with the present invention.

DETAILED DESCRIPTION OF THE PREFERRED EMBODIMENTS

Figure 1:
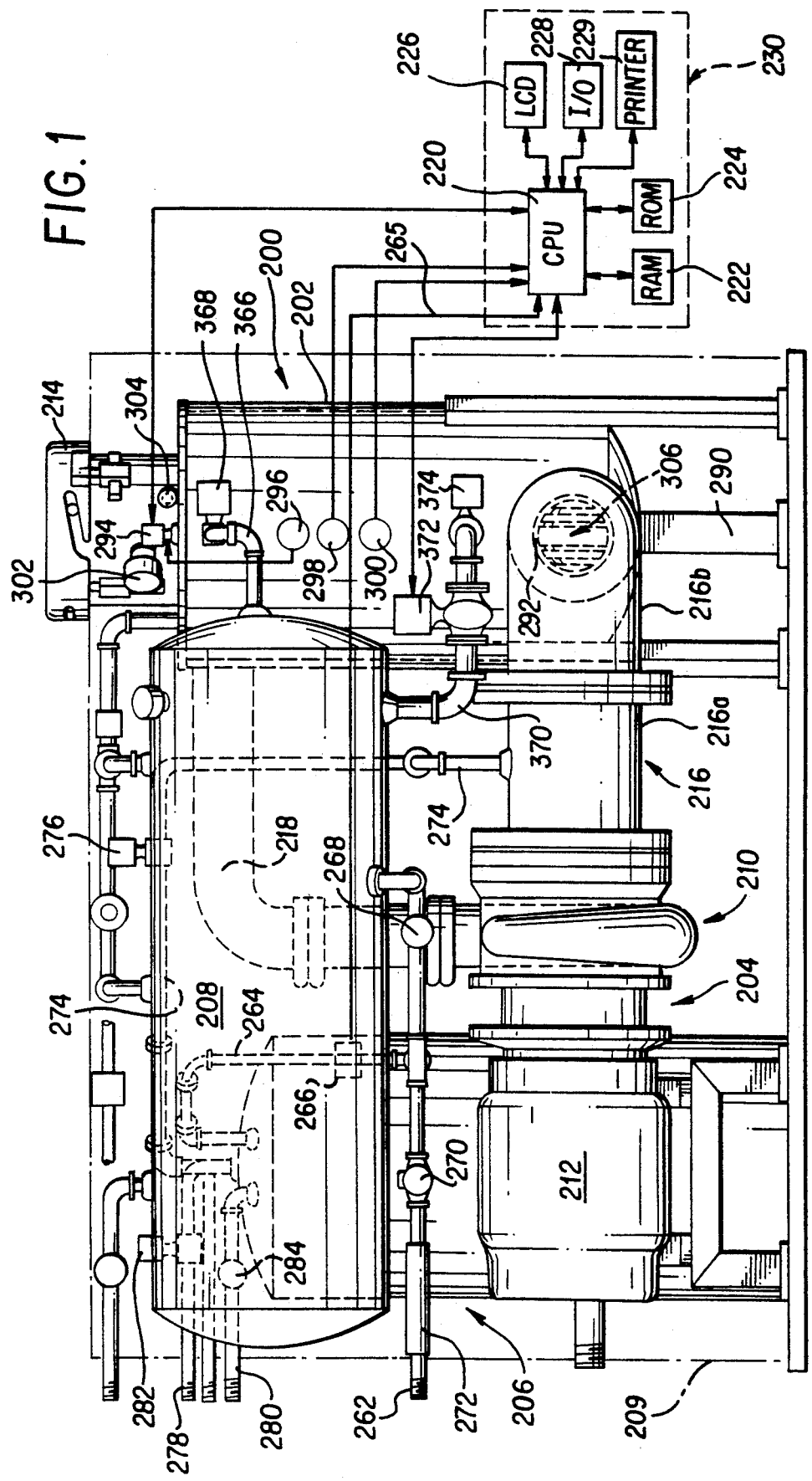
Figure 2:
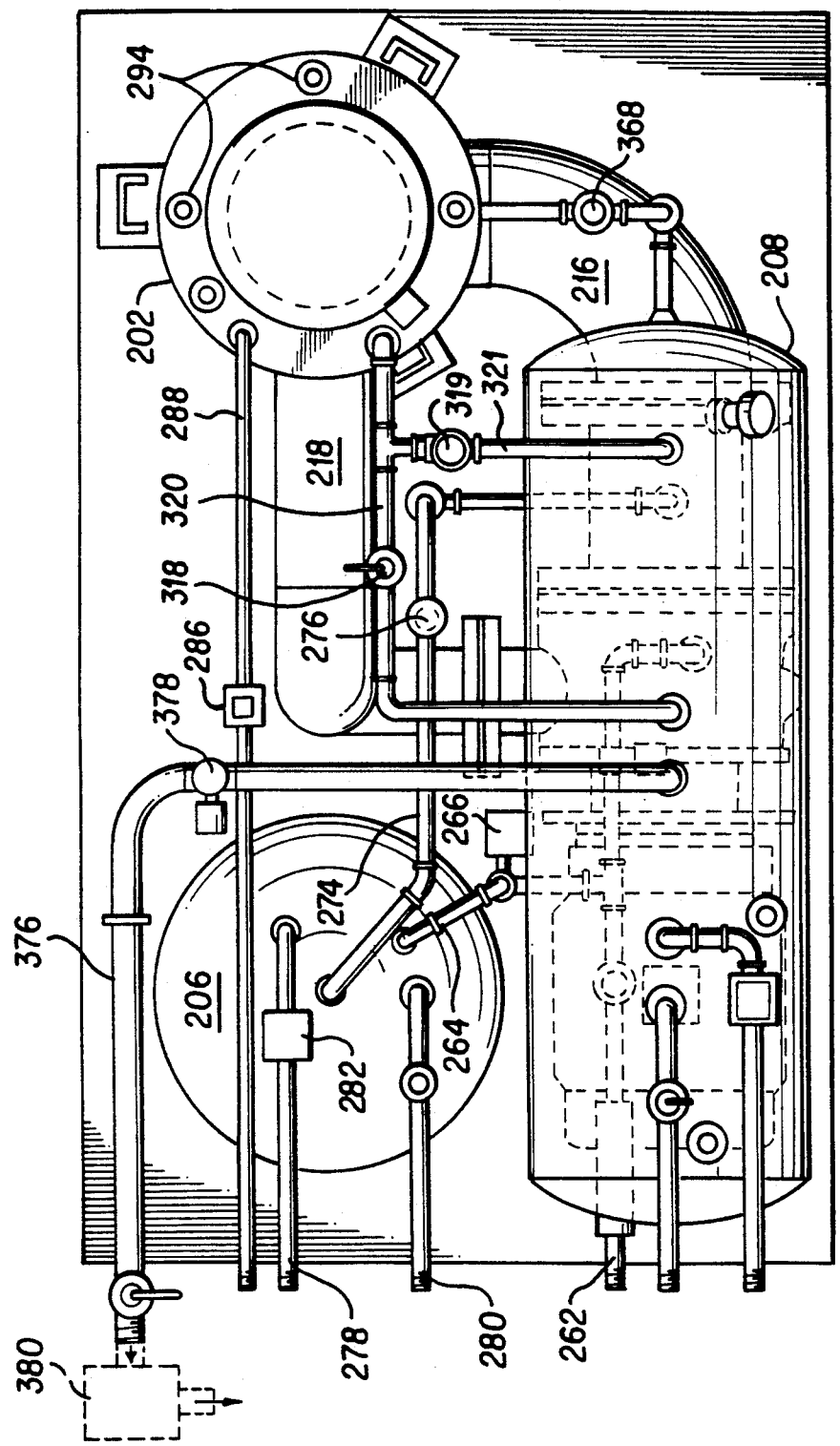
FIG. 2 is a top view of the apparatus depicted in FIG. 1.
Figure 3:
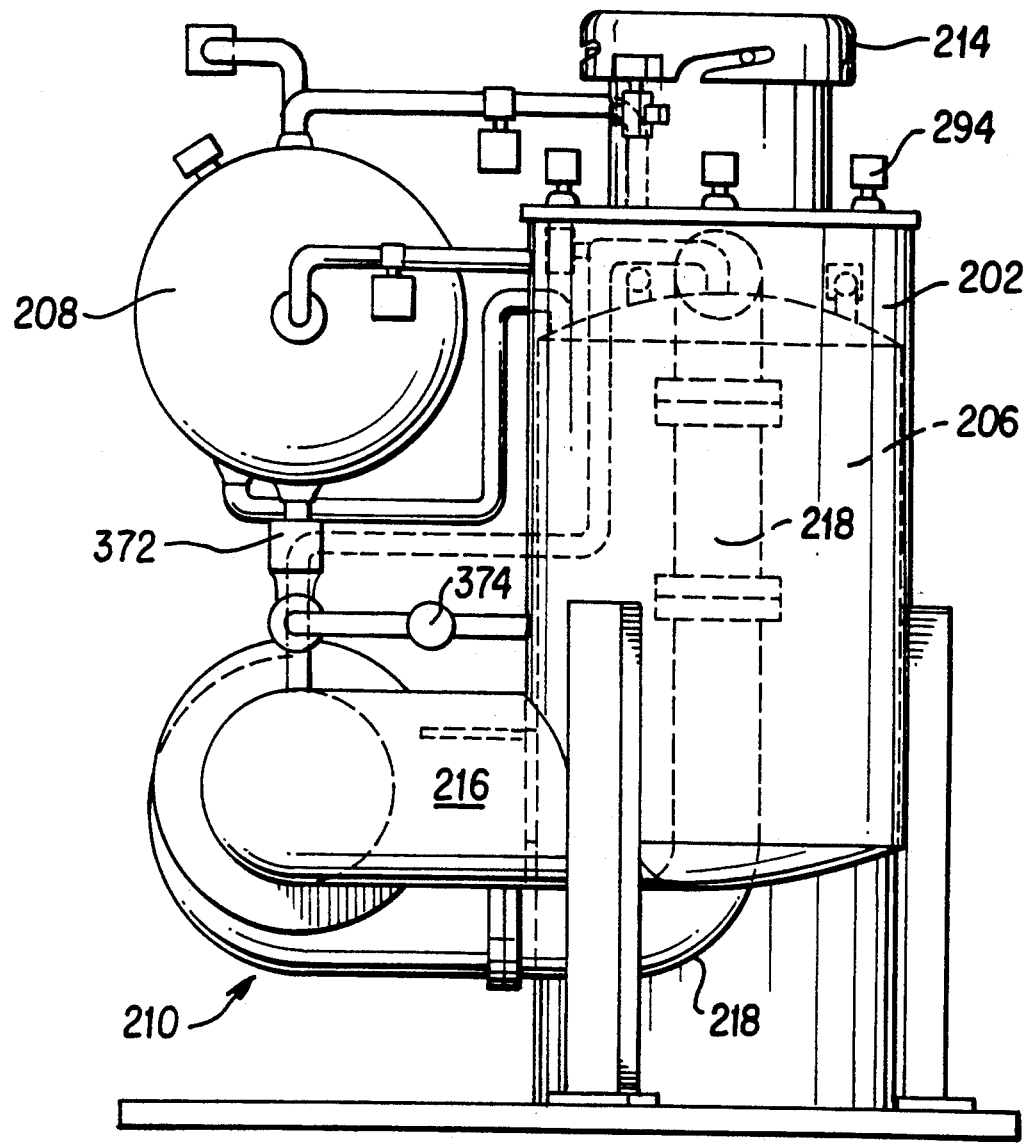
FIG. 3 is an end view of the apparatus depicted in FIG. 1.

With reference to the drawings, in like reference characters represent corresponding parts throughout the various views, and with particular reference to FIGS. 1 through 3, there is depicted a waste processing system in accordance with the teachings of the present invention, designated generally by reference character 200. The system 200 is comprised generally of a decontamination chamber 202, a waste processing chopper/pump assembly 204 ("chopper pump"), a fluid reservoir 206 for heating and storing a fluid such as water to be mixed with the waste to be processed, and a cooling tank 208 for receiving waste processed by the system and for cooling it prior to disposal. A housing 209 can optionally be provided to enclose the system and provide acoustic dampening. The chopper/pump 204 is generally comprised of a grinder assembly 210 and a motor assembly 212 for providing power to the grinder assembly. A removable cover 214 is provided over an inlet 215 of the decontamination chamber 202 to permit user access to the interior of the chamber for depositing waste to be treated by the processing system 200. The waste can be in the form of virtually any type of non-toxic inorganic or organic material, such as medical waste, food waste, rubber, plastics, and the like for which it is desirable to disinfect, or optimally render biologically neutral (i.e., biologically inert or devoid of living organisms) via sterilization. Medical waste can include, by way of non-limiting example, sharps such as needles, knives and blades, trocars, clamps, glass containers, gauze and bandages, surgical gloves and gowns, and various other instruments and paraphernalia which contacts internal body fluids such as blood, lymphatics, semen and vaginal fluids. Waste sterilization is preferred in instances such as with some forms of medical waste where bacteria, viruses and/or spores may be present, in which case all living organisms associated with the waste must be destroyed prior to its disposal.

The invention is particularly useful for effecting sterilization of virtually all forms of non-toxic waste by exposing the waste to superheated water at a temperature in the vicinity of from about 270° F. (132° C.) to about 275° F. (135° C.) at a pressure of from about 55 psi to about 65 psi, thereby assuring that the fluid is maintained substantially in a liquid state. Waste treatment with superheated liquid water as opposed to water vapor is preferred due to its greater ability to intermix with the waste solids as they are ground and circulated by the chopper/pump 204. As will be described in considerably greater detail below, waste processing is accomplished by way of a closed, pressurized circuit which includes the decontamination chamber 202, pump 204, chopper/pump inlet conduit 216, grinder assembly 210, and the pump outlet conduit 218 extending between the pump and the decontamination chamber. Accordingly, each of the circuit components is formed from suitable materials that are capable of withstanding the extremes of temperature, pressure and abrasion that are associated with operation of the waste processing system of the present invention.

The various aspects of system operation (i.e., temperature, pressure, material flow control and the like) are controlled by a control processor (CPU) 220. A random access memory (RAM) 222 is electrically connected to the CPU 220 and stores OSS (Operation System Software) software and provides working memory to the CPU. A read-only memory (ROM) 224 is also provided which stores various programs that are needed for input/output, power-up, self-test diagnostics, and the like for the CPU. A display 226 such as a liquid crystal (LCD), light emitting diode (LED) or cathode ray tube (CRT) display that is operable to provide human intelligible signal output to a system operator can optionally be provided. Various input/ output (I/O) means 228 such as keyboards, switches and the like are preferably provided to permit user input to the CPU. A printer 229 can optionally be connected to the CPU 220 to provide a printout of various data associated with operation of the waste processing system 200. All of the foregoing electronic components (CPU, I/O and the like) are preferably provided at a system control panel 230 that is readily accessible to the system user.

Figure 4:
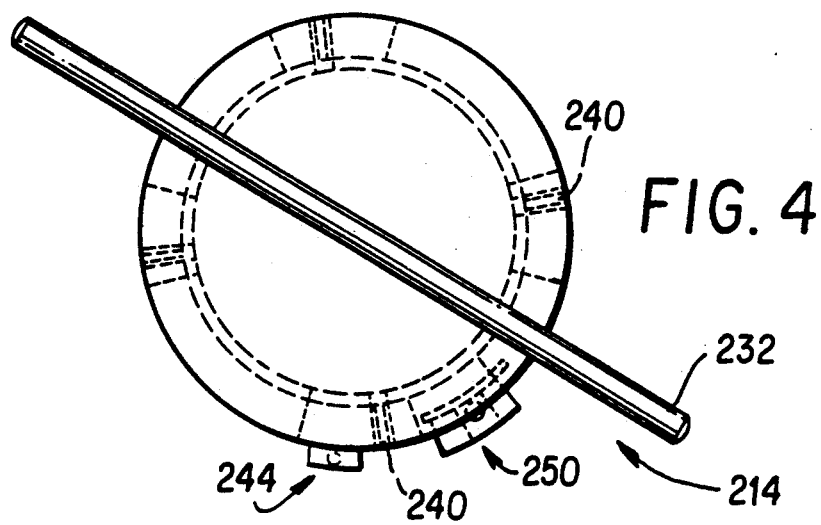
FIG. 4 is a top view of the waste decontamination chamber cover.
Figure 5:
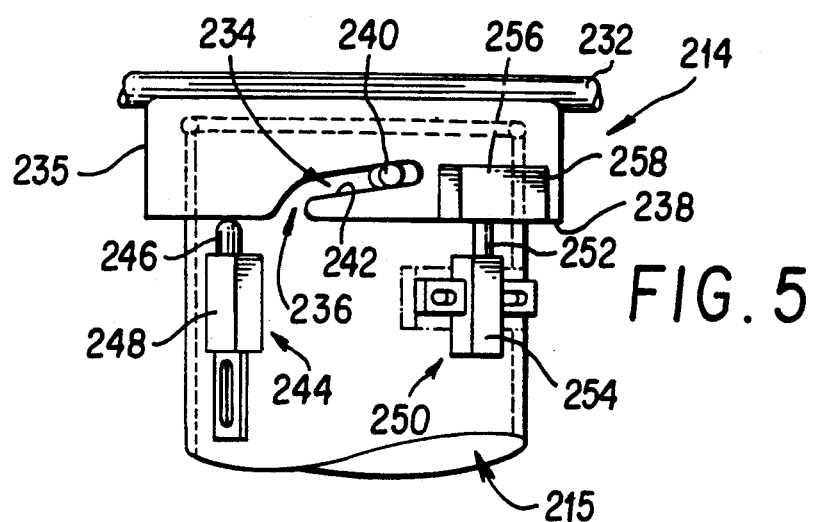
FIG. 5 is a side view of the cover and related cover locking hardware.

Waste material to be processed by the system is deposited in the decontamination chamber through the chamber inlet 215. As the waste material and water is to be exposed to relatively high pressure, the cover 214 is configured so as to withstand these pressures and to prevent inadvertent opening during the course of system operation. Details of the cover construction are depicted in FIGS. 4 and 5. An oversized handle 232 is provided which extends across the cover to facilitate user manipulation of the cover to attain the requisite level of decontamination chamber sealing. A slot 234 is provided at four equidistantly-spaced positions along the side 235 of the cover. Each slot 234 extends away from a slot opening 236 at the rim 238 of the cover in a direction that is counter to the direction of cover rotation to effect sealing of the decontamination chamber 202. The slots 234 are dimensioned to receive therein a corresponding key 240 which extends radially outwardly from the decontamination chamber outer surface adjacent to its inlet 215. Due to the rearward inclination of the slot 234, as the cover is rotated clockwise (i.e., toward a locked position in the depicted embodiment), each slot follows its correspondinglyreceived key 240, resulting in a downward exertion of pressure by the key 240 against the lower surface 242 of its corresponding slot.

A sensor 244 (FIG. 5) is provided along the chamber exterior adjacent to one of the keys 240. The sensor includes a plunger 246 that is reciprocably extensible with respect to a sensor housing 248. Biasing means such as a spring (not shown) received within the sensor housing 248 biases the plunger 246 outward from the housing 248 and into engagement with the cover rim 238. As the cover is rotatably advanced toward a closed position, the sensor plunger 246 (FIG. 5) is advanced into the housing 248 until it reaches a point within the housing that is commensurate with complete cover closure, at which point an electrical signal is emitted from the sensor 244 to the control processor 220. Upon receipt of the sensor signal, the processor 220 transmits a signal to a solenoid 250 near the chamber inlet 215 to effect extension of a latch 252 from the solenoid housing 254 and into a correspondingly-dimensioned recess 256 formed in a latch receptacle 258 mounted to the exterior surface of the side 235 of the cover. Extension of the latch into the latch receptacle 258 is required before processing of waste material can proceed so as to ensure user safety from not only contamination with potentially infectious waste, but also from physical harm which could result from exposure to processed waste solids as they are returned under pressure to the decontamination chamber 202 following grinding. As a further precaution, the solenoid 250 is of the type which requires electrical signal input to effect either retraction or extension of the latch 252. Accordingly, the cover 214 is constructed so as to be incapable of being opened by ordinary means during the course of waste processing as well as in the event of a system or power failure during a material processing cycle, thereby ensuring that the cover is not opened until processing has been completed.

With reference once again to FIGS. 1 through 3, uncontaminated (i.e., fresh or non-potable) water is supplied to the reservoir or pre-heat tank 206 via supply line 262 for subsequent use in the sterilization process. Water is conveyed from the supply line 262 into the pre-heat tank 206 by an inlet pipe 264 when a control valve 266 such as a solenoid valve positioned in the inlet pipe 264 (FIG. 2) is biased in an "open" position. The valve 266, as is the case with all remotely controllable valves and pumps used in the system of the present invention, communicate in a conventional manner with the CPU 220 and receive operating instructions therefrom as indicated by communication line 265 (FIG. 1), unless the specification explicitly or implicitly provides otherwise. Valve 266 is further operable to effect a pressure reduction in the incoming water stream from conventional inlet pressure (typically 60 psi) to about 8 psi. Another solenoid valve 268 is provided in the supply line 262 downstream from the pipe 264 to control water flow into the cool-down tank 208. The valves 266 and 268 are independently operable to provide for the control of fluid flow into their respective tank. A pressure relief valve 270 and fluid backflow preventer 272, as well as various other conventional plumbing apparatus that are conventionally used in fluid management, are also provided along the water supply line 262.

The pre-heat tank 206 is preferably in the form of a large capacity electric or gas-fueled water heater that is operable in a conventional manner, such as through the use of a thermostatically controlled burner or heater assembly, to maintain the stored water at an elevated, stand-by temperature of about 170° F. (77° C.) so as to expedite waste processing in the manner described below. A conduit 274 extends between the pre-heat tank 206 and the pump inlet conduit 216 to provide for the delivery of fluid from the pre-heat tank 206 to the flow of waste material en route to the pump grinder assembly 210 when the system 200 is in operation. Water flow through the conduit 274 is controlled by a solenoid valve 276 in accordance with CPU 220 signal output in the manner described above. A pair of ventilation outlets 278 and 280 extend from the upper end of the pre-heat tank 206. A solenoid valve 282 is positioned in the outlet 278 to provide for controlled venting of pressure within the pre-heat tank 206, whereas ventilation outlet 280 is provided with a mechanical pressure-responsive relief valve 284 that is operable in emergency situations to vent pressure from the tank 206 when the valve's trigger pressure has been attained. As the valve 284 does not communicate with the CPU 220, it is isolated from any problems that may arise with system electronics; instead, it is responsive solely to pressure exerted against it in its associated outlet 280.

The decontamination chamber 202 is configured as a pressurizable vessel that is capable of withstanding pressures in the range of from about 55 psi to about 65 psi. The chamber 202 can be formed from any suitable material that is capable of withstanding the extremes of temperature, pressure and abrasion that are associated with operation of the system. Suitable materials include, by way of example, stainless steel alloys and high impact, high temperature plastics. Prior to the commencement of waste processing, pressure within the decontamination chamber 202 can be equalized with atmospheric pressure to facilitate filling of the preheat and cool-down tanks 206 and 208. This can be accomplished by opening the normally closed solenoid control valve 286 in vent pipe 288 that extends from the decontamination chamber.

The decontamination chamber is oriented vertically as shown in the drawings to make use of gravity to assist in feeding of the waste to the pump assembly 204 and to minimize spatial demands. Tank support legs 290 can be provided to elevate the chamber above the ground and to position its outlet 292 at the lower end of the chamber at a level substantially even with that of the entrance to the pump inlet conduit 216.

With reference to FIGS. 1-3, a plurality of heaters 294 are provided at the upper end of the decontamination chamber 202 to provide for heating of the water from its elevated base temperature of about 170° F. (77° C.) as stored in the storage tank 206 to the optimal operating temperature of from about 270° F. (132° C.) to about 275° F. (135° C.) during the course of system operation in the manner set forth in detail below. The heaters are preferably in the form of electric resistance immersion heaters having a power output of about 5,000 watts each. However, the number and power output of the heaters 294 can be varied in accordance with such factors as the quantity and composition (i.e., solid, liquid, plastic, metal and so on) of the waste that is expected to be typically processed by a system user, as well as the rate of processing (i.e., system through-put) that is required by the user. The temperature and pressure within the decontamination chamber is sensed by respective temperature and pressure sensors 296 and 298, (FIG. 1) the output of which is directed to the CPU 220, which is operable to adjust various system operation parameters in the manner described below in instances where signal output from one or both of the sensors 296 and 298 is indicative of a measured value outside of a range of prescribed system limits. A further pressure sensor, designated by reference character 300, is provided with the decontamination chamber 202 to provide for deactivation of the fluid heaters 294 in the event that sensed pressure within the chamber exceeds a predetermined value. Output from the pressure sensor 300 is conveyed locally rather than through the CPU 220 to the heaters 294 in a manner known in the art (such as by way of circuit interruption to disable the supply of electric current to the heaters) to effect their deactivation. Fluid level sensors 302 and 304 are provided at the upper end of the decontamination chamber 202 to respectively monitor fluid levels within the chamber. Sensor 302 provides signal output to the control processor 220 to effect termination of the supply of water from the hot water tank 206 to the pump inlet conduit 216 when the decontamination chamber fluid level reaches a prescribed maximum. Sensor 304 is operable to provide signal output for deactivating the heaters 294 when the fluid level within the chamber 202 diminishes below a prescribed level.

Figure 6:
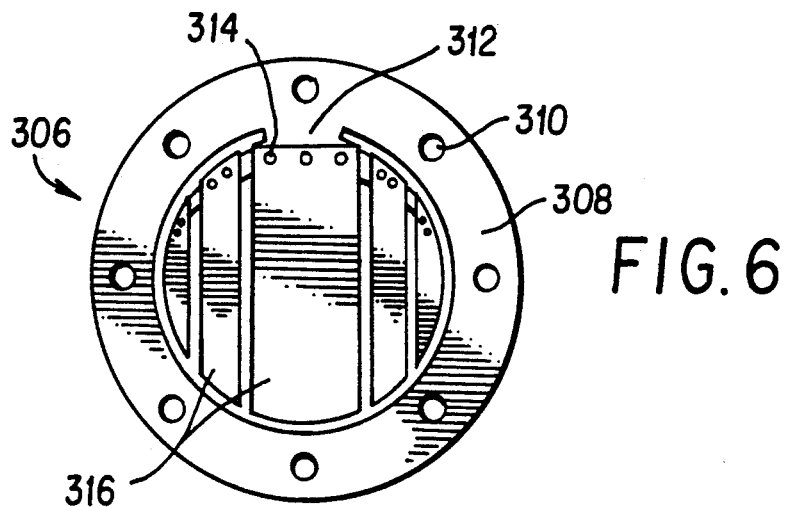
FIG. 6 is a frontal view of a waste control gate that can be positioned adjacent to the waste decontamination chamber outlet.

As noted above, waste from the decontamination chamber 202 passes from the chamber outlet 292 to the chopper/pump assembly 204 through pump inlet conduit 216. In the depicted embodiment, the conduit 216 is comprised of two sections 216a and 216b to accommodate the lateral displacement of the pump assembly 204 relative to the decontamination chamber; however, a greater or lesser number of sections can be provided in accordance with the system design. A gate 306 (FIGS. 1 and 6) is provided at the decontamination chamber outlet 292, preferably at the interface between the chamber outlet and the pump inlet conduit 216, to control the passage of waste to the pump assembly. The gate 306 is preferably constructed so that all of its moving parts are maintained within the sterilization fluid flow in order to ensure complete sterilization of the gate during the course of waste processing. With reference to FIG. 6, the gate 306 is shown as being comprised of a generally annular gasket 308 that is formed from a high temperature resistant material such as a "Viton" elastomer. A plurality of apertures 310 are provided about the annular periphery of the gasket to receive therethrough appropriate fasteners such as bolts or rivets (not shown) that are used to secure the gate between the chamber outlet 292 and the waste conduit 216. A gasket tab 312 extends radially inwardly from a portion of the gasket 308 to which is secured in a conventional manner, as by rivets 314 or a suitable temperature resistant adhesive, a plurality of vertically arrayed bars 316. Because the gate bars 316 are secured to the tab 312 independently of one another, each is free to independently move to permit for the passage of waste material through the gate and to the chopper/pump assembly 204. The gate bars 316 can be provided with a generally flat or curved surface contour in their downstream (i.e., facing the viewer) direction in accordance with user preference to facilitate receipt within the curved interior of the pump inlet 216. The bars are formed from a temperature resistant, hardened material such as stainless steel or any other suitably hard and temperature and abrasion resistant material and are spaced up to several mm. apart from one another to restrict passage of waste solids of a size in excess of the bar separation distance from passing through the gate to the pump assembly until the combination of fluid pressure upstream of the gate 306 (i.e., within the decontamination chamber 202) and vacuum pressure developed by operation of the chopper/pump assembly 204 as described below overcomes the inertia provided by the gate.

The chopper/pump assembly 204 can be of any suitable design which provides the requisite degree of waste material processing (i.e., grinding and chopping) and flow to accomplish the desired objective of processing of waste into relatively small fragments, thereby increasing its surface area for contact with high temperature water for effecting disinfection and optimally sterilization. In preferred aspects of system operation, the chopper/pump 204 is operable to process solid waste to a size in the range of from about 1/16 in. (1.5 mm) to about ¼ in. (6.5 mm) to not only facilitate its exposure to the heated fluid, but also to reduce waste volume. The family of horizontal endsuction chopper pumps manufactured by the Vaughan Co., Inc. of Montesano, Wash., such as the model VP3E pedestal pump, are particularly applicable for use in the present invention. Use of this family of pumps is advantageous, because their respective motors 212 are oil cooled and lubricated, thereby ensuring that waste contaminated water is confined to the prescribed waste and fluid circulation path. However, other motors which provide suitable amounts of torque, power, and confinement of the circulated fluid can be used.

Figure 8:
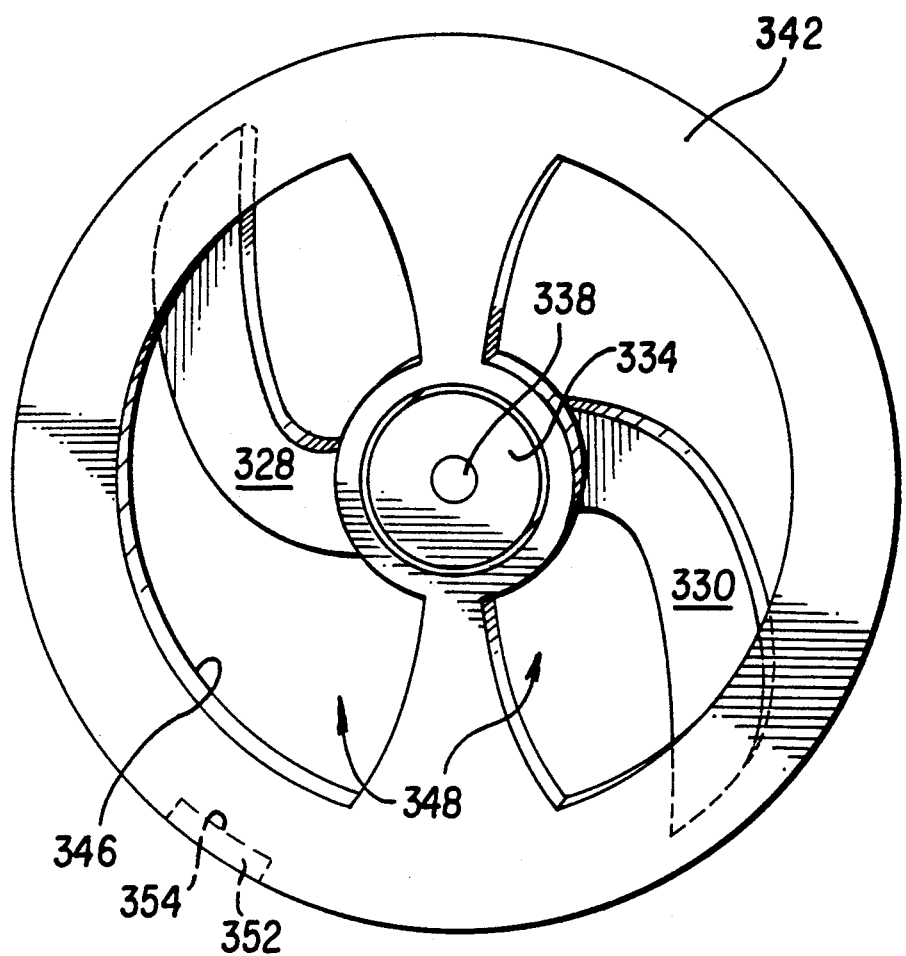
FIG. 8 is a frontal view of a portion of the system pump assembly.
Figure 7:
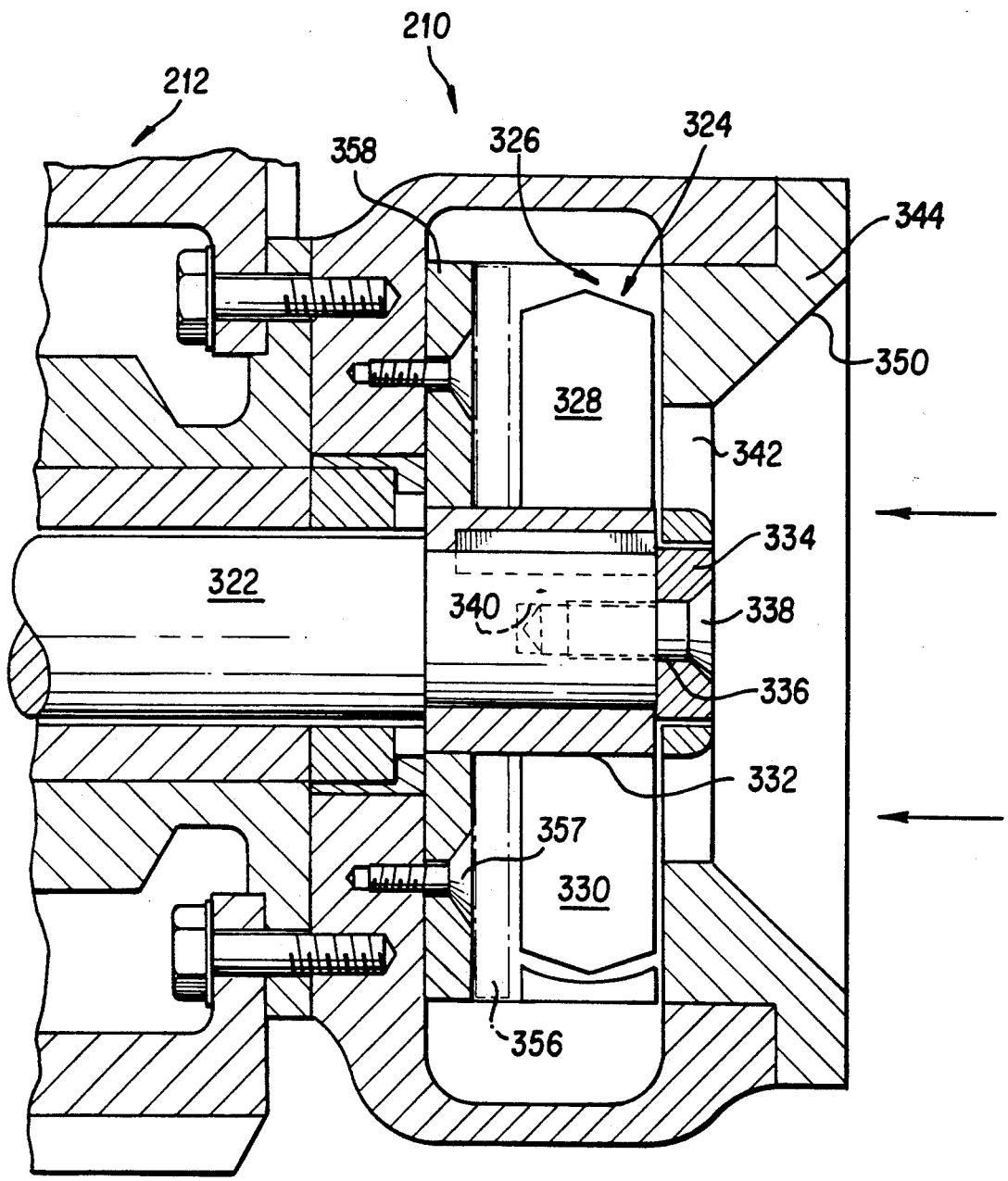
FIG. 7 is a sectional side view of a portion of the system pump assembly.

With particular reference to FIGS. 7 and 8, further details of the grinder and motor assemblies 210 and 212 are provided. The motor output shaft 322 extends into the grinder assembly 210 to provide rotational driving input (through an appropriate gear reduction assembly (not shown)) to an impeller 324 that is rotatably received within a venturi-shaped materials processing chamber 326. The impeller 324 includes a blade assembly that is comprised of a pair of generally opposed, curvalinear cutter blades 328 and 330 that extend from a hub 332. The hub is fixedly secured to the free end of the motor output shaft 322 by a retaining plate 334 having an aperture 336 through which extends a conventional fastener, such as the depicted threaded fastener 338. The fastener 338 is received within a complementary-threaded and dimensioned recess 340 formed in the motor shaft 322.

Positioned upstream (i.e., to the right side in FIG. 7) of the cutter blades 328 and 330 is a cutter plate 342 that is fixedly positioned with respect to the surrounding grinder housing 344. Alternatively, the cutter plate and grinder housing can be configured as a one piece, integral unit. The lower surface 346 of the cutter plate is provided with a hardened sharpened surface that is positioned in close proximity to the rotatably driven cutter blades 328 and 330 to provide for a compound cutting action of waste material that is interposed between the blades and the cutter plate surface. The cutting plate 342 defines a pair of laterally spaced elongated passages or apertures 348 through which waste material passes for cutting by the cutting blades 328 and 330. The housing 344 defines a wall 350 along its medial surface which extends radially outwardly in the upstream direction so as to guide waste material and fluid to the cutter blades. Cutting efficiency is further enhanced by the provision of a cutter block 352 (FIG. 8) along a portion of the inner periphery of the materials processing chamber 326. The radial inner edge 354 of the cutter block is provided with a sharpened surface which, together with the fixed cutting edge 346 of the plate 342, provides for enhanced cutting efficiency, as waste material is engaged, cut, and hurled forcefully thereagainst by the rotatably driven cutter blades 328 and 330. Cutting efficiency can be further augmented by the provision of an auxiliary cutting plate 356 (depicted in phantom in FIG. 7) downstream of the cutter blades which can be provided with any of a variety of suitable configurations which supplements the cutting effectiveness of the rotatably driven blades 328 and 330. The auxiliary plate can be fixedly secured by threaded fasteners 357 or other suitable fastening means to the base 358 of the materials processing chamber 324 as shown, or can be elevated and supported therefrom by appropriately dimensioned spacers (not shown) in instances where the auxiliary cutting plate is provided with cutting passages of the type described above with reference to cutting plate 342.

In one aspect of the invention, the motor is operable to rotate the blades 328 and 330 at a variety of different speeds (typically in the range of from about 1700 rpm to about 1900 rpm) in accordance with the waste composition (i.e., liquids, textiles, metals and so on) and such user-selectable parameters as flow rate through the system. Alternatively, a single motor speed can be provided for processing the waste without regard to its composition. Waste processing in both schemes of operation is to continue for so long as necessary to ensure that the waste is exposed to superheated water (i.e., temperature exceeding 270° F. (132° C.)) for a minimum of six minutes or longer in instances where waste sterilization is to be effected, as will be described in greater detail below. Because a variety of different types of waste are capable of being handled by the waste processing system of the present invention, all cutting surfaces are formed from suitably durable materials, such as hardened metal alloys and/or metals provided with a suitable chemical coating in a manner well known in the field of metallurgy.

With reference again to FIGS. 1 through 3, ground waste material and fluid processed by the grinder assembly 212 is urged through the materials processing chamber 326 to the decontamination chamber through grinder outlet 218, thereby providing a closed system for continued waste processing in the manner to be described below. During the course of system operation, the fluid heaters 294 are activated to elevate the temperature of the water and entrained waste material to the desired operation temperature (from about 270°

F. (132° C.) to about 275° F. (135° C.) to effect sterilization) and the pump 212 is operated for a period in excess of the requisite period of time that is accepted for effecting the desired disinfection or sterilization (in accordance with user instructions) in order to ensure sterilization of not only the waste material and fluid, but all of the waste processing hardware with which the waste and fluid comes into physical contact. The closed fluid path is maintained at a pressure of from about 55 psi to about 65 psi to ensure that the water introduced into the system for effecting sterilization maintains substantially a liquid state of matter. As mentioned above, sterilization with liquid water rather than water vapor is preferred to ensure full contact and penetration (where applicable) of waste solids to effect sterilization of even compact, porous materials such as textiles and gauze which can readily absorb potentially infectious bodily fluids. Excess pressure can be vented from this closed system into the cool-down tank through the operation of valves 318 and 319 (FIG. 2). Valve 318 is positioned in vent pipe 320 which extends between the decontamination chamber 202 and the cool-down tank 208 and is in the form of a self-actuating pressure relief valve that is operable to open and permit communication between the chamber and tank 208 once its set pressure has been attained. Valve 319, which is positioned in line 321 which branches from pipe 220 to the cool-down tank, is a solenoid valve under the control of the CPU 220 and is operable during the waste material cool-down cycle described below to release pressure from the decontamination chamber 202.

Once the prescribed period for waste sterilization in the system has passed, the sterilized liquid and entrained waste solids (collectively referred to as "waste mixture") are directed to the cool down tank 208 from the decontamination chamber 202 through inlet pipe 366. Flow into the inlet pipe 366 is controlled by solenoid valve 368, which is ordinarily biased in a closed position to prevent premature cooling of the waste material prior to completion of the required disinfection or sterilization cycle. As the waste mixture is received within the cool down tank 208, cool water contained within the tank 208 is admitted into the decontamination chamber 202 along conduit 370 (FIG. 1). A fluid pump 372 is provided in the conduit 370 to supply a pressurized flow of cooling water to the decontamination chamber. A valve 374 such as a ball valve is provided in the conduit to ensure unidirectional fluid flow into the decontamination chamber once the pump 372 has been activated. As the waste mixture is circulated by the pump assembly 204 throughout the closed system and cool down tank, the mixture is cooled from the temperature that was necessary to ensure the desired disinfection or sterilization to a temperature which satisfies any prevailing municipal requirements for waste disposal into, for example, a municipal sewer system. Once the temperature of the cooled waste mixture has diminished to the requisite disposal temperature, it is directed by the operation of pump 372 (FIG. 1) from the cool down tank, upon opening of solenoid valve 378, through a disposal conduit 376 (FIG. 2) for removal from the processing system. Preferably, the waste solids are separated from the liquid, as can be accomplished by filtration through filter assembly, depicted in phantom and denoted generally by reference character 380, prior to disposal, thereby reducing by several orders of magnitude the volume of waste solids to be disposed for many waste materials.

System Operation

Figure 9A:
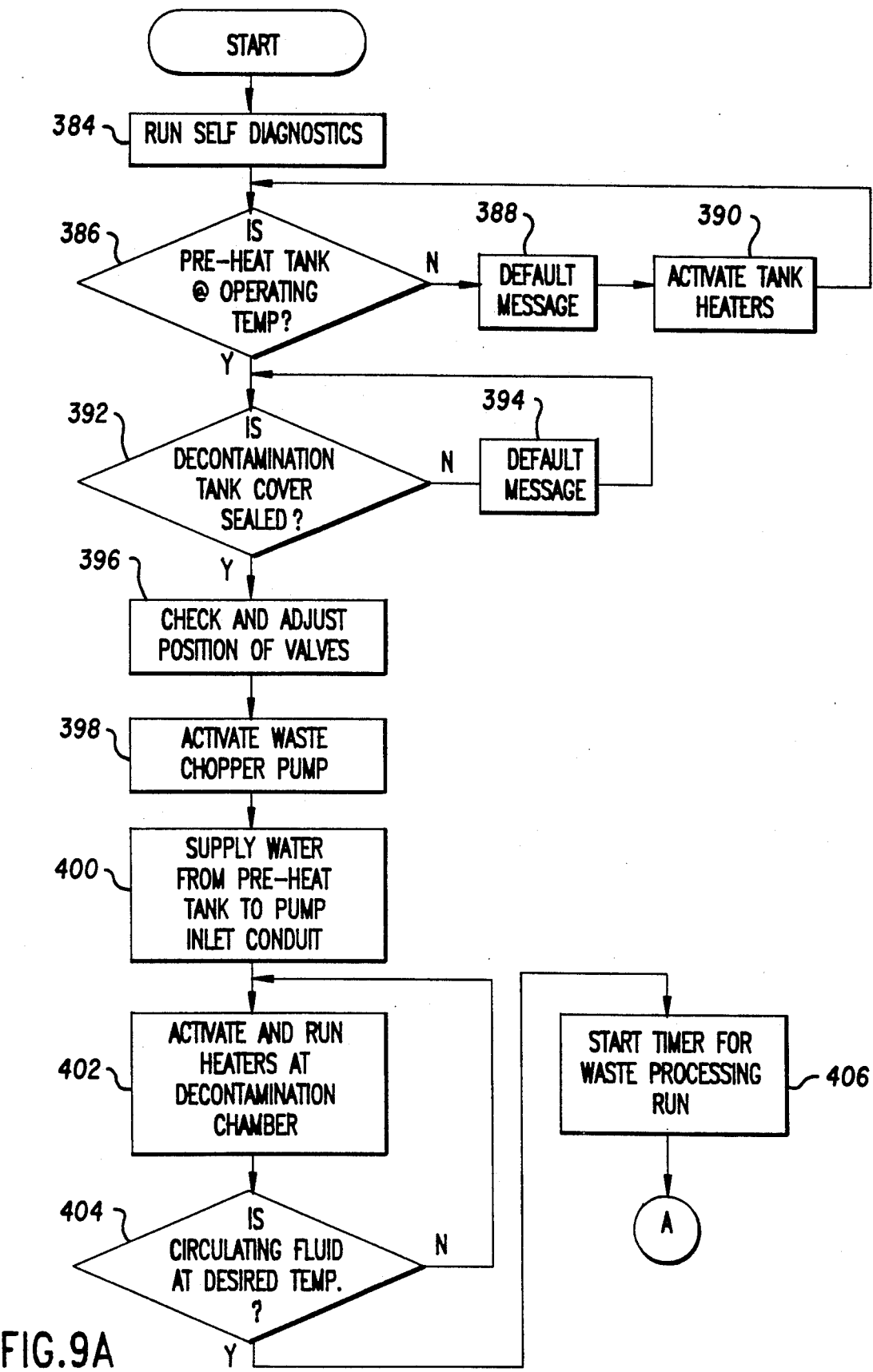
FIGS. 9A and 9B are flow diagrams of the operational control arrangement for the present invention.
Figure 9B:
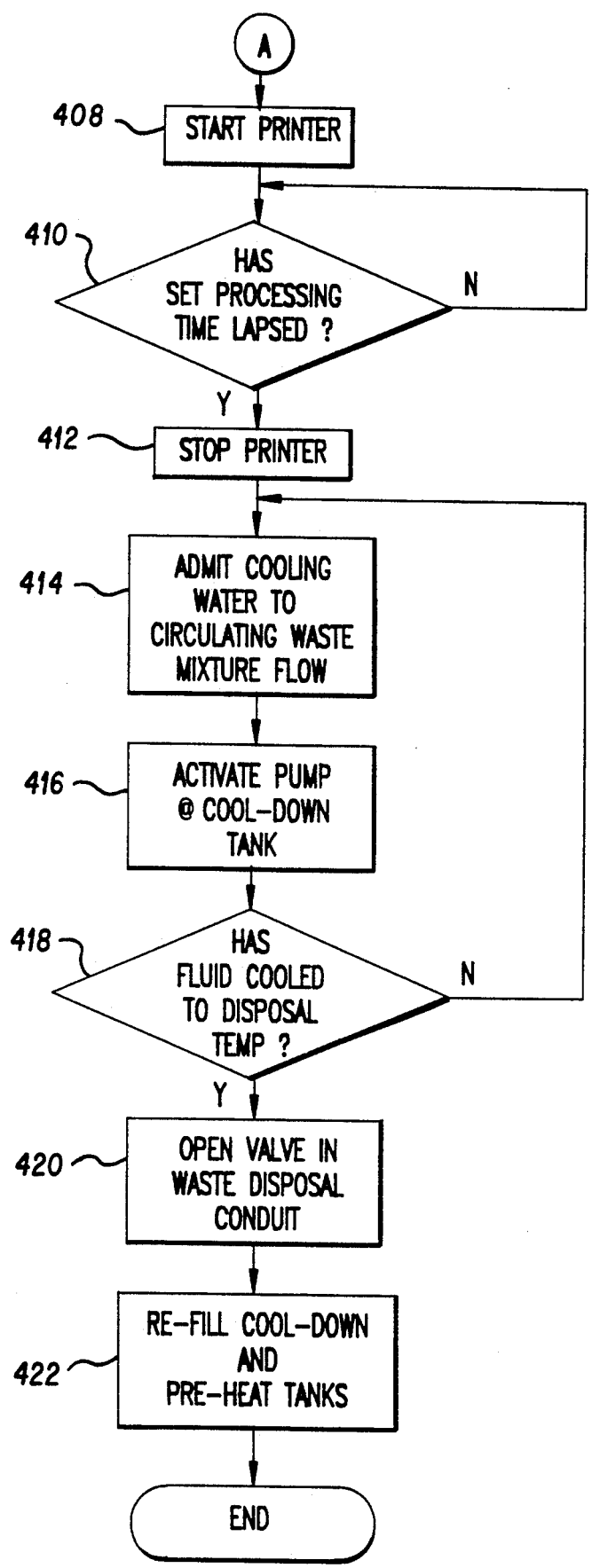

The operation of the waste processing system 200 of the present invention will now be described with reference to the flow diagram illustrated in FIGS. 9A and 9B, with concurrent reference to FIGS. 1 through 3.

Waste to be processed is deposited in the decontamination chamber 202 and the lid 214 therefor is closed and sealed. Prior to the commencement of waste processing, the CPU 220 is operable in accordance with program control from RAM to run a self-diagnostic check of the system electricals and electrically-operated components such as various valves and temperature and pressure sensors which communicate with the CPU, as indicated by block 384 in the flow chart. Communication between such electrically operable components and the CPU is indicated in FIG. 1 by a communication line extending between the controlled part and the CPU. An example of such a communication line is provided by line 265 which extends between valve 266 and the CPU 220. It is to be understood, however, that similar communication lines exist between the CPU 220 and each part of with which the CPU communicates, either in a unidirectional or a bi-directional manner. For the sake of clarity, however, such lines have not been included in FIG. 1, but they are understood to be present in order to provide the requisite control for system operation as described previously and below.

Upon successful completion of the self-diagnostic test, the CPU 220 receives signal input from a temperature sensor included with the pre-heat tank 206 that provides an indication of the temperature of fluid within the tank, as indicated by decision block 386. In instances where fluid temperature is below prescribed system operating limits for the system 200, as may be the case when the tank has recently been replenished with tap water, a "default" message conveying to the system user the unreadiness of the system to commence operation is produced in the display 226, as indicated by block 388, and the heating elements included with the tank are switched on to bring the fluid stored within the tank to operating temperature, noted by block 390.

In instances where the pre-heat tank fluid temperature meets the pre-established operating temperature, the CPU 220 is then commanded to analyze input from the decontamination chamber cover solenoid 254 (FIG. 5) to determine whether or not the cover 214 has been properly sealed, as shown by block 392. An appropriate default message such as "close cover" (block 394) is generated for display to the user via console display 226 in instances where output from the solenoid 254 to the CPU 220 along an appropriate communication line (not shown) is indicative of incomplete cover closure. If the output from the solenoid 254 is of a character that confirms cover closure and sealing, the CPU 220 is operable to communicate with the various valves and pumps under its control to confirm their respective proper orientation (i.e., "closed" or "open") prior to commencement of system waste handling (block 396) and to adjust the valves accordingly in instances where the valve position or pump operation status communicated to the CPU 220 does not comply with the system operating program stored in RAM 222.

Once the foregoing system operation statuses have been confirmed and corrected as required, the CPU 220 is operable to deliver signal input to the chopper/pump assembly 204 to effect chopper/pump operation at the prescribed rate of speed (block 398) and to deliver signal input to the valve 276 to permit a flow of heated fluid from the pre-heat tank 206 to the pump inlet conduit 216 (block 400). Fluid delivered from the tank 206 is conveyed by the chopper/pump 204 to the decontamination chamber 202 through pump outlet 218, where the fluid mixes with the waste material deposited therein. Once fluid pressure within the decontamination chamber 202, in combination with the negative pressure exerted by the chopper/pump 204, exceeds the inertia of the waste gate 306, waste solids pass with the fluid flow to the chopper/pump grinder assembly 210, where they are chopped and ground by the rotating cutter blades 329 and 330 and cooperating cutting surfaces of the cutter plate(s) 342 and 356, and conveyed into outlet 218 for recirculation to the decontamination chamber 202. Fluid level sensor 302 provides signal output to the CPU to convey the fill status of the decontamination chamber as water is delivered from the pre-heat tank into the circulating stream of water and liquid and solid waste material in the manner described above.

As the fluid and waste mixture is circulated between the decontamination chamber and chopper/pump through the respective pump inlet and outlet conduits 216 and 218, the CPU 220 is operable to activate the decontamination chamber heaters 294 (Block 402) to elevate the temperature of the circulating stream to the operating temperature that is required to effect the selected level of processing. In this regard, a temperature in the range of 270° F. is to be maintained for a continuous period of at least six minutes to effect waste sterilization, whereas a lesser temperature on the order of at least about 212° F. is preferred for disinfection. Temperature data from the decontamination chamber is conveyed by sensor 296 to the CPU, which continues signal output to the heaters 294 (block 404) until the fluid temperature as sensed by sensor 296 reaches the desired operating temperature. Once this temperature has been attained, a timer (not shown) such as that typically provided for CPU operation is started, as noted by block 406. Additionally, a printer, which can optimally be provided with the system to document such system parameters as fluid temperature, is also actuated (block 408).

As the waste processing cycle continues in the foregoing manner, the CPU is operable to compare clock and temperature sensor 296 output data with the preselected time and temperature parameters stored in CPU memory to allow for determination of whether the required time of material processing at the requisite temperature set forth in the CPU operating program has lapsed (block 410). This comparison process continues until the clock and temperature data provided to the CPU 220 indicate that the requisite period has passed, at which time the printer is deactivated (block 412) and the CPU is operable to effect cooling of the water and entrained waste solids and liquids ("waste mixture") as indicated by block 414.

The CPU 220 implements cooling of the waste mixture by directing valve 374 in the cooling tank conduit 370 to open and pump 372 to commence pumping of cool (i.e., ambient temperature or chilled) water into the decontamination chamber 202, as indicated by block 416. The CPU 220 also commands valve 368 in inlet 366 to open, thereby admitting a portion of the circulating waste mixture with the cool-down tank 208. The CPU monitors the temperature of the circulating waste mixture (block 418) and continues to supply cool water until the temperature diminishes to the desired level for disposal. The desired cooling temperature may, for example, be that temperature established by municipalities at which qualifying waste material can be passed into the sewer or other municipal disposal system. Once the temperature has reached the requisite cool-down temperature, the CPU 220 directs waste valve 378 in disposal conduit 376 to open (block 420), thereby allowing for the disposal of the cooled waste mixture from the cool-down tank 206. Waste solids in excess of a predetermined size can optionally be filtered from the waste mixture passing through the disposal conduit to permit its disposal apart from the liquid component of the waste mixture. Such waste solids, by virtue of having been processed in the foregoing manner, can be disposed of in a conventional manner in a compact form, thereby lessening the burden on waste disposal facilities and on the waste originator in providing for safe and efficient waste disposal. The CPU is operable thereafter to provide for refilling of the respective pre-heat and cool-down tanks (Block 422) to replenish their supplies of water used in the foregoing processing cycle. Tank refilling is accomplished as a result of CPU signal input to valves 266 and 268 directing their respective opening, thus allowing for replenishment of associated pre-heat and cool-down tanks 206 and 208 with fresh water for use in a subsequent waste processing cycle.

What is claimed is:

1. A waste processing system, comprising:
   a receptacle for receiving waste material and a liquid to be mixed with the waste material, said receptacle having an inlet and a waste outlet;
   a pump for chopping the waste material and circulating and mixing the liquid and waste material, said pump having a pump inlet and an outlet;
   a waste inlet conduit extending between said waste outlet and said pump inlet;
   a waste outlet conduit extending between said pump outlet and said receptacle inlet, said receptacle, pump, waste inlet and waste outlet conduits defining a closed, pressurized waste processing circuit through which the mixed liquid and waste material can be circulated; and
   a heating system operable to heat the mixture of the liquid and the waste material to a temperature in excess of the boiling point of the liquid at standard pressure, said temperature being sufficient to effect biological neutralization of the mixed liquid and waste material, all surfaces of said waste processing system with which the waste material comes into contact being processed to attain said biological neutralization.

2. The system according to claim 1, wherein the heating system comprises a liquid heater that is mounted within the receptacle.

3. The system according to claim 1, wherein the liquid comprises water and the heating system is operable to heat the liquid to a temperature of at least about 100° C.

4. The system according to claim 1, wherein said heating system comprises at least one temperature sensor operable to sense the temperature of the liquid and closed, pressurized waste material mixture circulating through said waste processing circuit.

5. The system according to claim 1, further comprising a processed waste storage receptacle.

6. The system according to claim 5, wherein said processed waste storage receptacle is coupled to said closed, pressurized waste processing circuit through a selectively operable valve.

7. The system according to claim 5, wherein said processed waste storage receptacle includes a discharge outlet.

8. The system according to claim 7, further comprising a waste solids filter positioned adjacent to said discharge outlet, said waste solids filter being operable to retain processed waste solids of a predetermined minimum size prior to discharge from the waste storage receptacle.

9. The system according to claim 1, further comprising a waste solids restrainer positioned within said closed, pressurized waste processing circuit, said waste solid restrainer being operable to inhibit downstream passage of waste solids in excess of a predetermined size until a predetermined pressure has been attained within said closed, pressurized waste processing circuit.

10. The system according to claim 9, wherein said waste solids restrainer comprises a plurality of pivotably displaceable strips.

11. The system according to claim 1, wherein said receptacle comprises a removable cover, said removable cover and said receptacle comprising a mutually engageable locking system that is operable to inhibit cover removal until waste has been processed for a prescribed time interval.

12. The system according to claim 1, further comprising a control system operable to receive temperature input data from said mixture of waste material and liquid circulating through said closed, pressurized waste processing circuit and to operate said pump for a prescribed time interval once said sensed temperature has attained a prescribed level.

13. The system according to claim 12, further comprising a processed waste receptacle and a selectively operable valve assembly mounted within a processed waste conduit extending between said processed waste receptacle and said closed, pressurized waste processing circuit, said control system being operable to move said valve assembly between an open position and a closed position.

14. The system according to claim 13, wherein said processed waste receptacle includes an outlet and a selectively actuatable valve assembly mounted in communication with said receptacle outlet, said control system being operable to move said selectively actuatable valve assembly between an open position and a closed position.

15. The system according to claim 13, further comprising a cooling fluid inlet conduit coupled to said closed, pressurized waste processing circuit, said control system being operable to selectively effect delivery of cooling fluid through said cooling fluid inlet conduit and into said closed, pressurized waste processing circuit.

16. The system according to claim 15, wherein said cooling fluid inlet conduit is coupled to a municipal water supply.

17. The system according to claim 12, wherein said control system is capable of operating said heating system to attain a temperature for the circulating mixture of waste material and liquid that is sufficient to effect sterilization of the mixture.

18. The system according to claim 12, wherein said heating system includes at least on fluid heater that is operable in accordance with signal input from said control system to maintain the liquid within the receptacle at a prescribed, elevated temperature.

19. A process for biologically neutralizing waste material, comprising the steps of:
providing waste material to be biologically neutralized;
grinding waste material to form particles of a predetermined maximum size;
mixing the ground waste material with a liquid and circulating the liquid and entrained waste material through a closed, pressurized waste processing circuit; and
heating and circulating the liquid-waste material to an elevated temperature in excess of the boiling point of the liquid at standard pressure, said elevated temperature being sufficient to effect biological neutralization of the waste material, all surfaces of said waste processing system with which said waste material comes into contact being processed to attain said biological neutralization.

20. The system according to claim 19, wherein the liquid comprises water and the liquid-waste mixture is heated to a temperature of at least 100° C. at a pressure which substantially inhibits transformation of the liquid into vapor.

21. The system according to claim 19, wherein the liquid-waste mixture is heated to a prescribed temperature that is maintained for a predetermined time interval that is sufficient to effect sterilization of the mixture.

22. The system according to claim 19, wherein the processed waste material is discharged into a municipal waste removal system.

23. The system according to claim 22, wherein waste solids of a minimum prescribed size are separated from the liquid-waste mixture prior to discharge.

24. The system according to claim 22, wherein the temperature of the processed waste material is reduced following waste processing and prior to discharge.

25. The system according to claim 24, wherein said temperature reduction is accomplished by mixing a relatively lower temperature fluid with the processed liquid-waste mixture.

26. The system according to claim 25, further comprising the step of generating a record of liquid-waste mixture temperature and processing time.

27. The system according to claim 26, wherein said record is rendered in a tangible form.

28. The system according to claim 19, further comprising the step of inhibiting access to the waste material until the prescribed level of biological neutralization has been attained.

29. The system according to claim 19, further comprising the step of generating human intelligible indicia indicative of the status of waste processing.

30. A system for processing waste to a prescribed level of biological inactivity, comprising:
a receptacle for receiving waste material, the receptacle having a re-sealable cover, a fluid inlet, and a fluid outlet;
means for reducing the dimensions of the waste material and for mixing the reduced waste material with a processing liquid to form a liquid-waste mixture;
means for circulating the liquid-waste mixture within a closed, pressurized circuit including said receptacle and said waste dimension reducing means;
means for heating the liquid-waste mixture to a prescribed temperature above the boiling point of the liquid at standard pressure; and control means for implementing selective operation of said waste dimension reducing means, said circulating means, and said heating means to effect waste processing at the prescribed temperature for a prescribed time interval to effect biological neutralization of the waste material and all surfaces of the waste processing system with which the waste material comes into contact.

31. The system according to claim 30, wherein the heating means is operable to heat the liquid-waste mixture within the closed, pressurized circuit.

32. The system according to claim 31, wherein said control means comprises at least one temperature sensor operable to provide signal output that is indicative of liquid-waste mixture temperature within the closed, pressurized circuit.

33. The system according to claim 32, further comprising means for discharging processed waste into a municipal waste removal system.

34. The system according to claim 32, further comprising means for separating waste solids of a predetermined minimum size from the processed liquid-waste mixture.

35. The system according to claim 32, further comprising means for reducing processed liquid-waste mixture temperature and for disposing of at least a portion of said processed liquid-waste mixture following attainment of a prescribed maximum liquid-waste temperature value.

36. The system according to claim 35, wherein said temperature reducing means comprises means for admitting a cooling liquid into said closed pressurized circuit.

37. The system according to claim 30, further comprising a processed waste storage receptacle.

38. The system according to claim 30, wherein said receptacle comprises means for inhibiting cover removal upon initiation of a waste processing cycle until said waste processing cycle has been completed.

39. The system according to claim 38, wherein said cover removal inhibiting means comprises a solenoid reciprocably extendible within a recess formed within said re-sealable cover.

40. The system according to claim 30, wherein said waste dimension reducing means and said liquid-waste mixture circulating means comprises a rotatably drivable impeller mounted within said closed, pressurized circuit.

41. The system according to claim 30, wherein said control means is operable to effect heating of said liquid-waste mixture to a temperature of at least about 100° C.

42. The system according to claim 41, wherein said control means is operable to effect heating of said liquid-waste mixture to a temperature in the range of from about 130° C. to about 135° C. while said system is maintained at a pressure sufficient to substantially inhibit vapor formation.

* * * * *

UNITED STATES PATENT AND TRADEMARK OFFICE
CERTIFICATE OF CORRECTION

PATENT NO. : 5,277,869

DATED : 11 January 1994

INVENTOR(S) : Sanford A. GLAZER et al.

It is certified that error appears in the above-identified patent and that said Letters Patent is hereby corrected as shown below:

```
Column 16
In claims 20, 21, 22, 23, 24, 25, 26, 27, 28 and 29, line 1
of each, change "system" to -- process --.
```

Signed and Sealed this

Thirteenth Day of June, 1995

Attest:

BRUCE LEHMAN

*Attesting Officer*     *Commissioner of Patents and Trademarks*